United States Patent [19]

Pinkus

[11] Plant 4,655

[45] Feb. 24, 1981

[54] PEPEROMIA PLANT AVONELL

[76] Inventor: Ralph Pinkus, 7423 Lavendale, Dallas, Tex. 75230

[21] Appl. No.: 91,243

[22] Filed: Nov. 5, 1979

[51] Int. Cl.[3] ..... A01H 5/12

[52] U.S. Cl. ..... Plt./88

[58] Field of Search ..... Plt./88

*Primary Examiner*—Robert E. Bagwill

[57] ABSTRACT

A peperomia having a narrow cream margin.

1 Drawing Figure

BACKGROUND OF THE NEW PLANT

This plant is a mutant of *Peperomia caperata* 'Emerald Ripple.' The mutation occurred in our greenhouse in Wylie, Tex. The first mutation was propagated asexually and was fairly stable in the foliage colors. Continued propagation and selection has produced over four hundred (400) uniform, true to form plants. Occasional reversion occurs rarely.

DESCRIPTION OF THE DRAWING

This new variety of peperomia plant is illustrated by the accompanying full color photographic drawing which shows the plant at a mature stage of growth. The leaf coloration shown is believed to be as nearly true as it is reasonably possible to obtain by conventional professional photographic standards and procedures.

DESCRIPTION OF THE PLANT

The following is a detailed description of my new variety of peperomia plant with color specification according to Exotica Third Horticultural Color Guide published by Roehrs Company, Rutherford, N.J., the observations having been made at Dallas, Tex.

The Plant

Origin: Mutation.
Parentage: *Peperomia caperata* 'Emerald Ripple'.
Classification: Piperaceae.
Form: Herbaceous.
Height: 6 inches.
Growth: Low, bushy house plant.
*Stem size.*—2 to 4 inches in length, $\frac{1}{4}$–$\frac{3}{8}$ at base. Basal stems very close to ground.
Foliage: Quantity abundant. One (1) leaflet per stem. Petiole arises from basal stem.

*Leaf size.*—Generally 1 inch to 2 inches long. 1 to $1\frac{3}{4}$ inches wide.
*Leaf shape.*—Cordate, undulate at margins, deeply quilted. Carmine petiole.
*Ribs & veins.*—Venation—palmate.
*Rachis.*—Normal.
Color: Upperside Pine Green #68—with silver overlay, changing to narrow band along margin of Cream #1+; in immature foliage Amethyst #46 at petiole attachment. Underside—Seafoam #71+; center Cream #1 edge.

The Flower

Blooming habit: January to April.
Borne: Unbranched spike.
Size: Spike 6 inches to 8 inches tall.
Shape: Spike erect.
Petalage: Insignificant.
*Texture.*—Slightly sticky.
*Appearance.*—Spike pendulous when past.
*Persistence.*—After about 3 weeks, spike drops off.
Petaloids: Apetalous.
Discoloration: None.
Fragrance: None.

Brief Description of "family" Information

This new variety of peperomia plant most nearly resembles *Peperomia caperata* 'Emerald Ripple Variegata.' It differs from the former in that the cream margin is not as wide and the former has no amethyst color at petiole attachment. This is a foliage plant.

I claim:

1. A new and distinctive variety of peperomia plant substantially as herein shown and described, characterized by a unique silver green cream margined leaf, with amethyst coloration at petiole attachment which is altogether new.

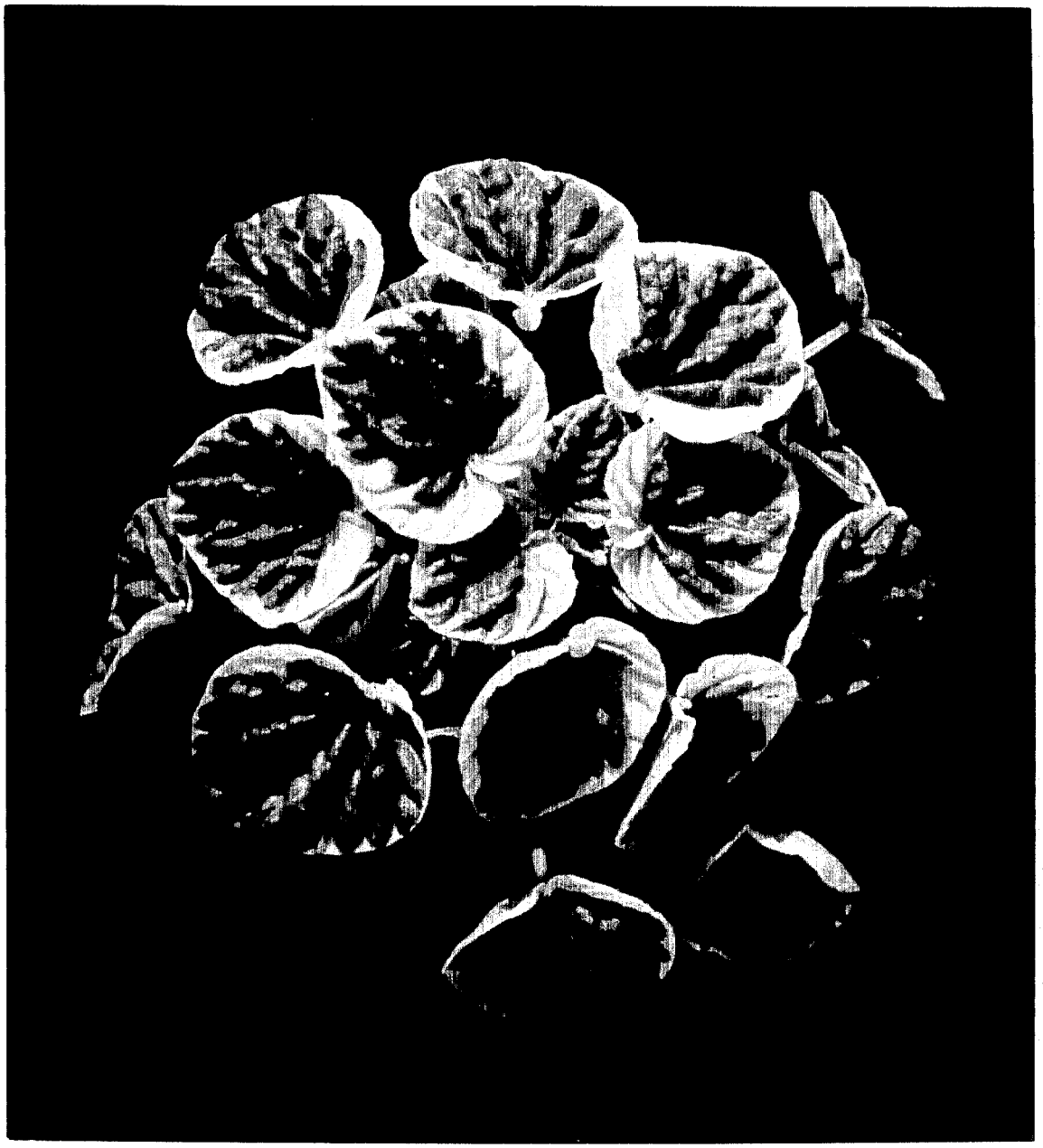

* * * * *